(12) United States Patent
Kim et al.

(10) Patent No.: US 9,460,548 B2
(45) Date of Patent: Oct. 4, 2016

(54) METHOD AND APPARATUS FOR DISPLAYING MEDICAL IMAGE

(71) Applicant: SAMSUNG MEDISON CO., LTD., Gangwon-do (KR)

(72) Inventors: Han-jun Kim, Gangwon-do (KR);
Sung-yoon Kim, Gangwon-do (KR);
Jun-sang Yoo, Gangwon-do (KR);
Jun-kyo Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 78 days.

(21) Appl. No.: 14/073,312

(22) Filed: Nov. 6, 2013

(65) Prior Publication Data
US 2014/0139518 A1 May 22, 2014

(30) Foreign Application Priority Data

Nov. 20, 2012 (KR) .................. 10-2012-0131954

(51) Int. Cl.
*G06T 15/08* (2011.01)
*G06T 15/06* (2011.01)
(Continued)

(52) U.S. Cl.
CPC ............. *G06T 15/08* (2013.01); *A61B 8/466* (2013.01); *A61B 8/467* (2013.01); *A61B 8/483* (2013.01);
(Continued)

(58) Field of Classification Search
CPC .............. A61B 6/466; A61B 6/5223; A61B 2019/5289; A61B 5/7425; A61B 6/022; A61B 5/743; A61B 8/463; A61B 8/523; A61B 8/483; A61B 8/466; G06T 19/00; G06T 2210/41; G06T 15/08; G06T 2219/008; G06T 2219/028; G06T 15/00; G06T 19/003; G06T 15/20; G06T 17/10; G06T 3/0037; G06F 3/011; G06F 3/017; G06F 3/013; G06F 3/0304; G06F 19/325; G06F 3/04815; G06F 3/04845; G06F 3/005; G06F 3/04842; G06F 3/0485; G06F 3/0487; G06F 3/04883; G06F 19/321; G06F 3/01; G06F 3/016; G06F 3/0482; G06F 17/3026

See application file for complete search history.

(56) References Cited

U.S. PATENT DOCUMENTS 7,349,563 B2 * 3/2008 Kiraly .................. G06T 15/06
128/922
2004/0210138 A1 10/2004 Murashita et al.
(Continued)

FOREIGN PATENT DOCUMENTS

DE    10 2009 024571 A1    12/2009
EP       1 523 939 A1       4/2005
(Continued)

OTHER PUBLICATIONS

European Search Report issued in European Application No. 13187529.6-1660 dated Mar. 18, 2014.
(Continued)

*Primary Examiner* — Sultana M Zalalee
(74) *Attorney, Agent, or Firm* — McDermott Will & Emery LLP

(57) ABSTRACT

Disclosed is an apparatus for displaying a medical image, the apparatus including: a data acquisition unit for acquiring volume data of an object; an image generation unit for generating a medical image, which includes at least one three-dimensional (3D) stereoscopic image and at least one 2D stereoscopic image generated based on at least one of a direction, a gradient, and a depth of an object shown in the 3D stereoscopic image, from volume data of the object; and a displaying unit for displaying the generated medical image.

19 Claims, 6 Drawing Sheets

(51) Int. Cl.
*H04N 13/02* (2006.01)
*H04N 13/04* (2006.01)
*A61B 6/03* (2006.01)
*A61B 8/08* (2006.01)
*A61B 8/00* (2006.01)
*A61B 5/055* (2006.01)

(52) U.S. Cl.
CPC ............... *A61B 8/523* (2013.01); *G06T 15/06* (2013.01); *H04N 13/0239* (2013.01); *H04N 13/0275* (2013.01); *H04N 13/0452* (2013.01); *A61B 5/055* (2013.01); *A61B 6/032* (2013.01); *A61B 6/037* (2013.01); *A61B 8/0866* (2013.01); *A61B 8/463* (2013.01); *G06T 2210/41* (2013.01)

(56) References Cited

U.S. PATENT DOCUMENTS

| | | | |
|---|---|---|---|
| 2005/0024724 A1* | 2/2005 | Kim et al. | 359/462 |
| 2005/0122343 A1* | 6/2005 | Bailey et al. | 345/619 |
| 2005/0187474 A1 | 8/2005 | Kwon | |
| 2005/0289472 A1* | 12/2005 | Morita et al. | 715/757 |
| 2006/0034513 A1 | 2/2006 | Cai et al. | |
| 2006/0173338 A1 | 8/2006 | Ma et al. | |
| 2009/0147073 A1 | 6/2009 | Getty | |
| 2009/0310846 A1* | 12/2009 | Lemchen | 382/132 |
| 2010/0091097 A1* | 4/2010 | Pockett | H04N 13/0018 348/54 |
| 2011/0235066 A1 | 9/2011 | Sakuragi | |
| 2012/0075303 A1 | 3/2012 | Johnsson et al. | |
| 2014/0035910 A1 | 2/2014 | Wakai et al. | |

FOREIGN PATENT DOCUMENTS

| | | |
|---|---|---|
| JP | 2003 325525 A | 11/2003 |
| JP | 2011-206167 A | 10/2011 |
| JP | 2012-217633 A | 11/2012 |
| WO | 2006 059668 A1 | 6/2006 |
| WO | 2012 137947 A1 | 10/2012 |

OTHER PUBLICATIONS

Korean Office Action dated Jul. 31, 2014 issued Korean Patent Application No. 10-2012-0131954 (English translation).
Korean Notice of Final Rejection issued in corresponding Korean Patent Application No. 10-2012-0131954, mailed on Feb. 25, 2015; 6 pages with English translation.

* cited by examiner

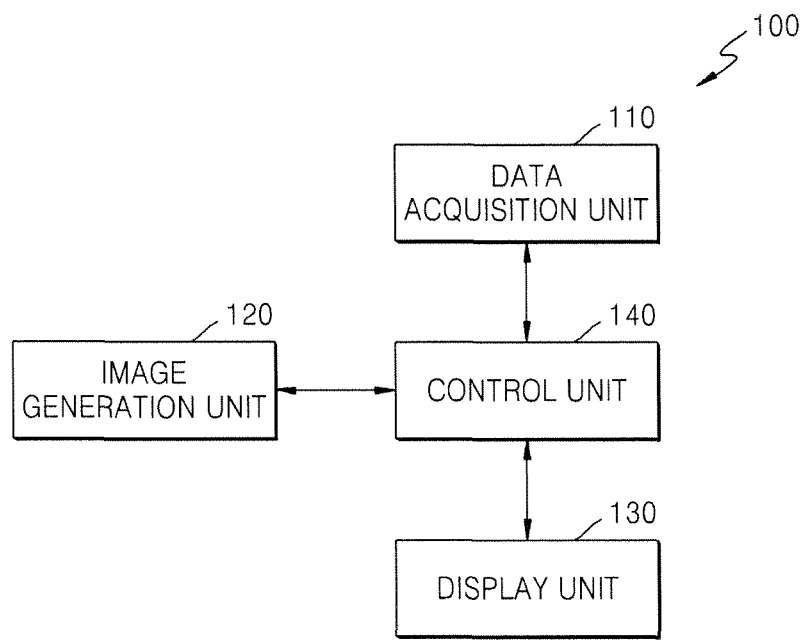
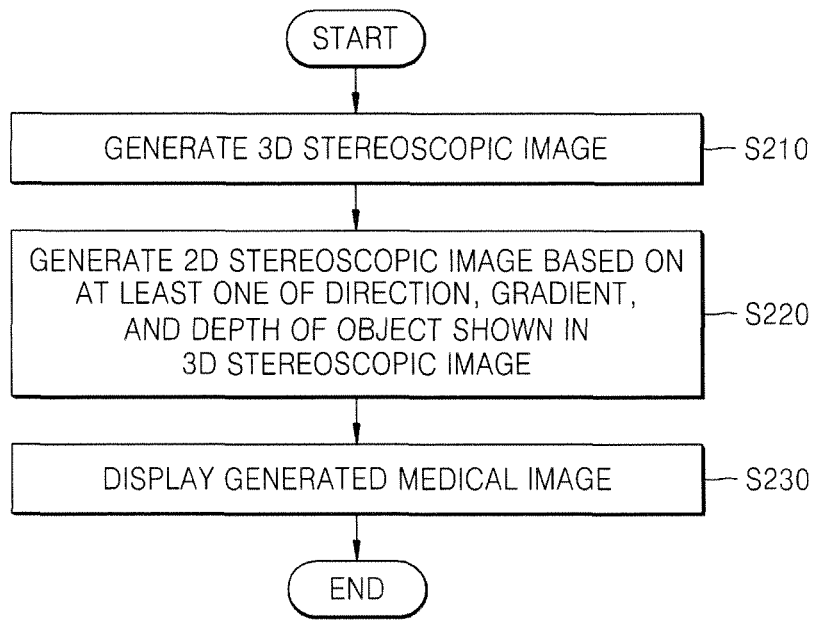

METHOD AND APPARATUS FOR DISPLAYING MEDICAL IMAGE

CROSS-REFERENCE TO RELATED PATENT APPLICATION

This application claims the benefit of Korean Patent Application No. 10-2012-0131954, filed on Nov. 20, 2012, in the Korean Intellectual Property Office, the disclosure of which is incorporated herein in its entirety by reference.

BACKGROUND OF THE INVENTION

1. Field of the Invention

The present invention relates to a method and apparatus for displaying a medical image, and more particularly, to a method and apparatus for displaying a stereoscopic medical image by providing a medical diagnosis image in the form of a stereoscopic image so that a user has depth perception.

2. Description of the Related Art

Ultrasound diagnosis apparatuses using ultrasound waves are widely used in a medical field for obtaining information on the inside of a target object because of noninvasive and nondestructive diagnostic characteristics. Since ultrasound diagnosis apparatuses can provide images of internal tissues of the human body to medical practitioners in real-time without observing technology that is invasive to human tissue, such as a surgical operation, the ultrasound diagnosis apparatuses are very important in the medical field. Ultrasound diagnosis apparatuses are used to generate two-dimensional (2D) or 3D diagnosis images of a shape of the inside of a target object.

An ultrasound diagnosis apparatus generally uses a conversion element formed of a piezoelectric material to transmit and receive an ultrasound signal. The ultrasound diagnosis apparatus generates an ultrasound signal to be transmitted to a human body by electrically stimulating the conversion element and transmits the ultrasound signal to the human body. The ultrasound signal transmitted to the human body is reflected from an edge of human tissue, and an ultrasound echo signal reflected from the edge of the human tissue to the conversion element is converted to a high-frequency signal. The ultrasound diagnosis apparatus generates an ultrasound image of the tissue by amplifying and processing the converted high-frequency signal.

However, the ultrasound diagnosis apparatus, which displays only 2D ultrasound images indicating a cross section of a target object, cannot provide vivid ultrasound images to a user.

SUMMARY OF THE INVENTION

The present invention provides a stereoscopic image allowing a user to have depth perception.

According to an aspect of the present invention, there is provided a method of displaying a medical image, the method including: generating a medical image, which includes at least one three-dimensional (3D) stereoscopic image and at least one 2D stereoscopic image based on at least one of a direction, a gradient, and a depth of an object shown in the 3D stereoscopic image, from volume data of the object; and displaying the generated medical image. The generating of the medical image may include generating the 2D stereoscopic image based on at least one of a direction, a gradient, and a depth of a plane corresponding to the cross section in the 3D stereoscopic image, wherein the 2D stereoscopic image indicates at least one cross section of the object.

The method may further include receiving a user's input, wherein the generating of the medical image includes generating a non-stereoscopic image corresponding to at least one of the 3D stereoscopic image and the 2D stereoscopic image, and the displaying of the generated medical image includes displaying a stereoscopic image instead of a non-stereoscopic image which is being displayed, or displaying a non-stereoscopic image instead of a stereoscopic image which is being displayed, based on the user's input.

The generating of the medical image may include rendering a plurality of 3D stereoscopic images by setting a virtual camera in a virtual space where the object is located and changing a direction of ray casting towards the object from the virtual camera.

The generating of the medical image may include generating a medical image including a non-stereoscopic image of the object. The displaying of the generated medical image may include determining a type and the number of images to be displayed according to a user's input. The generating of the medical image may include generating a plurality of 3D stereoscopic images in which at least one of a direction, a gradient, and a depth of the object shown in the plurality of 3D stereoscopic images is different, and the displaying of the generated medical image may include displaying at least one of the plurality of 3D stereoscopic images based on the user's input.

The 2D stereoscopic image may include stereoscopic images of a cross section of the object, which is selected based on a user's input from the 3D stereoscopic image. The 2D stereoscopic image may include a stereoscopic image of three cross sections of the object, which are orthogonal to each other, or a stereoscopic image of a curve-shaped cross section of the object.

According to another aspect of the present invention, there is provided an apparatus for displaying a medical image, the apparatus including: a data acquisition unit for acquiring volume data of an object; an image generation unit for generating a medical image, which includes at least one three-dimensional (3D) stereoscopic image and at least one 2D stereoscopic image generated based on at least one of a direction, a gradient, and a depth of an object shown in the 3D stereoscopic image, from volume data of the object; and a displaying unit for displaying the generated medical image. The image generation unit may generate the 2D stereoscopic image based on at least one of a direction, a gradient, and a depth of a plane corresponding to the cross section in the 3D stereoscopic image, and wherein the 2D stereoscopic image indicates at least one cross section of the object.

The image generation unit may generate the 2D stereoscopic image based on at least one of a direction, a gradient, and a depth of a plane corresponding to the cross section in the 3D stereoscopic image, wherein the 2D stereoscopic image indicates at least one cross section of the object.

The apparatus may further include a reception unit for receiving a user's input, wherein the image generation unit further generates a non-stereoscopic image corresponding to at least one of the 3D stereoscopic image and the 2D stereoscopic image, and the display unit may display a stereoscopic image instead of a non-stereoscopic image which is being displayed, or a non-stereoscopic image instead of a stereoscopic image which is being displayed, based on the user's input.

The image generation unit may render a plurality of 3D stereoscopic images by setting a virtual camera in a virtual space where the object is located and changing a direction of ray casting towards the object from the virtual camera.

The image generation unit may generate a medical image further including a non-stereoscopic image of the object.

The apparatus may further include a reception unit for receiving a user's input, wherein the display unit determines a type and the number of images to be displayed according to a user's input.

The image generation unit may generate a plurality of 3D stereoscopic images in which at least one of a direction, a gradient, and a depth of the object shown in the plurality of 3D stereoscopic images is different, and the display unit may display at least one of the plurality of 3D stereoscopic images based on the user's input.

The apparatus may further include a reception unit for receiving a user's input, wherein the image generation unit generates the 2D stereoscopic image including a stereoscopic image of a cross section of the object, which is selected based on a user's input from the 3D stereoscopic image.

The image generation unit may generate the 2D stereoscopic image including stereoscopic images of three cross sections of the object, which are orthogonal to each other.

The image generation unit may generate the 2D stereoscopic image including a stereoscopic image of a curve-shaped cross section of the object.

According to another aspect of the present invention, there is provided a non-transitory computer-readable storage medium having stored therein program instructions, which when executed by a computer, perform the method.

BRIEF DESCRIPTION OF THE DRAWINGS

The above and other features and advantages of the present invention will become more apparent by describing in detail exemplary embodiments thereof with reference to the attached drawings in which:

FIG. 1 is a block diagram of an apparatus for displaying a medical image, according to an embodiment of the present invention;

FIG. 2 is a flowchart illustrating a method of displaying a medical image, according to an embodiment of the present invention;

DETAILED DESCRIPTION OF THE INVENTION

Figure 3A:
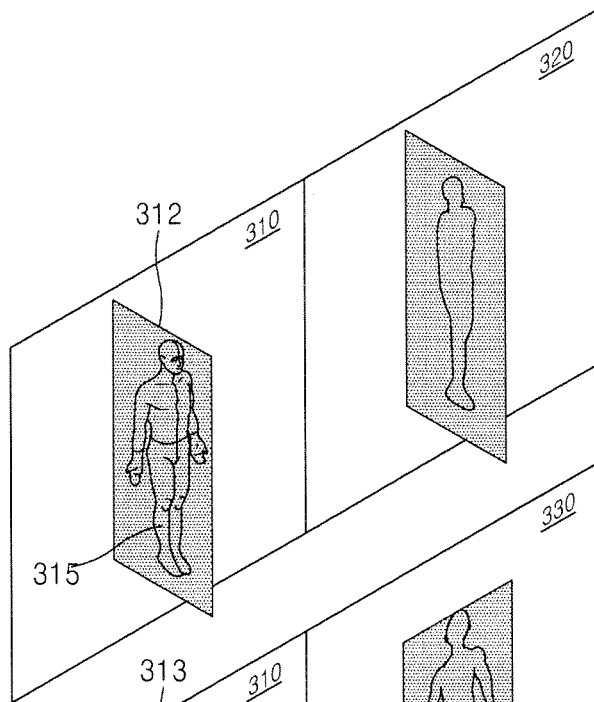
FIGS. 3A to 3C illustrate a medical image displayed according to an embodiment of the present invention.

Although general terms as currently widely used as possible are selected as the terms used in the present invention while taking functions in the present invention into account, they may vary according to an intention of one of ordinary skill in the art, judicial precedents, or the appearance of new technology. In addition, in specific cases, terms intentionally selected by the applicant may be used, and in this case, the meaning of the terms will be disclosed in a corresponding description of the invention. Accordingly, the terms used in the present invention should be defined not by simple names of the terms but by the meaning of the terms and the contents over the present invention.

In the specification, when a certain part "includes" a certain component, this indicates that the part may further include another component instead of excluding another component unless there is different disclosure. In addition, the term, such as " . . . unit" or the like, disclosed in the specification indicates a unit for processing at least one function or operation, and this may be implemented by hardware, software, or a combination thereof.

As used herein, expressions such as "at least one of," when preceding a list of elements, modify the entire list of elements and do not modify the individual elements of the list.

In the specification, the term "object" may indicate a part of a human body. For example, the object may include an organ, such as the liver, the heart, the womb, the breast, the abdomen, or the like, a fetus, or the like, or may include any one cross section of the human body. In the specification, the term "user" may be a medical practitioner, a nurse, a medical pathologist, a medical image expert, or the like as a medical expert but is not limited thereto. In addition, the term "stereoscopic image" in the present invention indicates a cubic image allowing a viewing person to have depth perception by using disparity between both eyes and includes a still image and a video image. Technology for implementing the stereoscopic image includes all commercialized stereoscopic image technologies and may include any other stereoscopic image technologies to be implemented in the future.

An apparatus for displaying a medical image according to an embodiment of the present invention may be widely applied to not only ultrasound images but also magnetic resonance imaging (MRI) devices, computed tomography (CT) devices, positron emission tomography (PET) devices, and the like for displaying medical images for disease diagnosis by restoring a cross section and volume data of human tissue from a signal projected to the human tissue.

FIG. 1 is a block diagram of an apparatus 100 for displaying a medical image, according to an embodiment of the present invention.

Referring to FIG. 1 the apparatus 100 according to an embodiment of the present invention may include a data acquisition unit 110, an image generation unit 120, and a display unit 130. The shown components will now be described one by one.

The data acquisition unit 110 may acquire volume data of an object. The term "volume data" may indicate data including spatial information and clinical information, such as an anatomical shape and the like, of the object. For example, an ultrasound system transmits an ultrasound signal towards the object, receives an ultrasound signal reflected by the object i.e., an ultrasound echo signal, and generates volume data by using the received ultrasound echo signal. The data acquisition unit 110 may include a probe (not shown) for transmitting and receiving an ultrasound signal and a beamformer (not shown) for performing transmission beamforming and reception beamforming of the ultrasound signal. In addition, the data acquisition unit 110 may acquire volume data of the object, which is stored in a memory (not shown), from the memory.

The image generation unit 120 may generate a medical image including at least one three-dimensional (3D) stereoscopic image and at least one 2D stereoscopic image from the volume data acquired by the data acquisition unit 110. The 2D stereoscopic image may be generated based on at least one of a direction, a gradient, and a depth of the object shown in the 3D stereoscopic image.

The display unit 130 may display the medical image generated by the image generation unit 120. Thus, a user may easily perceive a bending degree, a relative position difference, a relative direction, and the like between components of the object from the medical image including at least one 3D stereoscopic image and at least one 2D stereoscopic image of the object.

The apparatus 100 according to an embodiment of the present invention may further include a control unit 140. The control unit 140 commonly controls a general operation of the apparatus 100. For example, the control unit 140 may generally control the data acquisition unit 110, the image generation unit 120, and the display unit 130 by executing programs stored in the memory.

A method of displaying a medical image by using the components in the apparatus 100 will now be described in detail with reference to FIG. 2.

FIG. 2 is a flowchart illustrating a method of displaying a medical image, according to an embodiment of the present invention.

Referring to FIG. 2, the method according to an embodiment of the present invention may include operations processed by the apparatus 100 shown in FIG. 1. Thus, although omitted below, the above description of the apparatus 100 shown in FIG. 1 is applied to the method of FIG. 2.

In operation S210, the apparatus 100 generates a 3D stereoscopic image from volume data of an object. For example, the apparatus 100 may generate a stereoscopic image by rendering the volume data. The term "rendering" indicates technology for displaying a 2D projection image of a 3D discretely sampled data set, such as volume data. A method of rendering the volume data includes a ray casting method of detecting a part of an object, which reflects light, by irradiating virtual light beams on the object. To render a 2D projection image of a 3D discretely sampled data set, a virtual camera in a virtual space where an object is located should be defined, and an opacity and color of each voxel should be defined. Operation S210 may be performed by the image generation unit 120. A method of generating the 3D stereoscopic image will be described below in detail with reference to FIGS. 7A and 7B.

In operation S220, the apparatus 100 generates a 2D stereoscopic image based on at least one of a direction, a gradient, and a depth of the object shown in the generated 3D stereoscopic image. Operation S220 may be performed by the image generation unit 120. The term "2D stereoscopic image" indicates an image that is a 2D image of the object but allows a user to have depth perception by being displayed in a stereoscopic method. For example, the generated 2D stereoscopic image may show at least one cross section of the object. That is, the 2D stereoscopic image may be a cross-sectional stereoscopic image showing a one cross section of the object in a stereoscopic method so that the user has depth perception. In addition, the image generation unit 120 may generate a 2D stereoscopic image based on at least one of a direction, a gradient, and a depth of a plane where a predetermined cross section is located in the object shown in the generated 3D stereoscopic image. In a spherical coordinate system associated with the object, the terms "direction", "gradient", and "depth" may indicate an angle formed against a z axis of a positive direction, an angle formed against an x axis of a positive direction based on the z axis, and a distance r from the center point, respectively.

In addition, operations S210 and S220 may be performed at the same time or in a reversed order. In addition, the method according to an embodiment of the present invention may generate a medical image including not only a stereoscopic image of the object but also a non-stereoscopic image of the object. That is, a medical image displayed in the method according to an embodiment of the present invention may include both a stereoscopic image and a non-stereoscopic image.

In operation S230, the apparatus 100 displays a medical image including the 3D stereoscopic image and the 2D stereoscopic image generated in operations S210 and S220. Operation S230 may be performed by the display unit 130. The apparatus 100 may determine a type and the number of images to be displayed according to a user's input.

A medical image which may be generated and displayed in the method according to an embodiment of the present invention will now be described with reference to FIGS. 3A to 5.

Figure 3B:
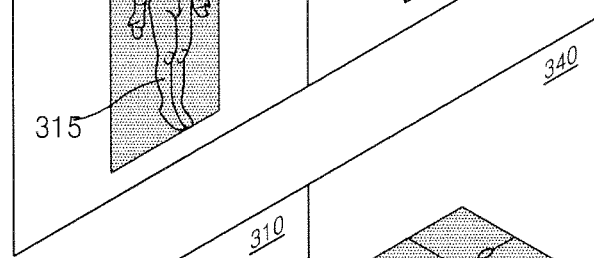
Figure 3C:
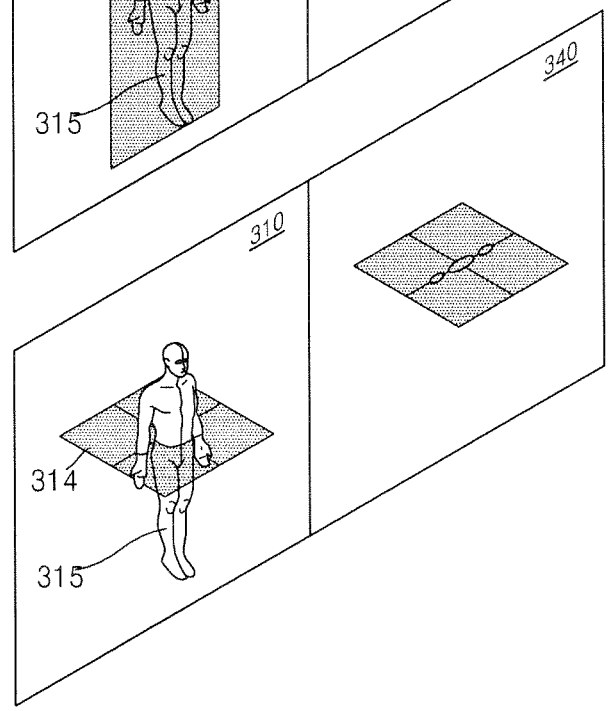

FIGS. 3A to 3C illustrate a medical image displayed according to an embodiment of the present invention.

As shown in FIGS. 3A to 3C, a medical image displayed by the apparatus 100 according to an embodiment of the present invention may include a 3D stereoscopic image 310 of an object 315. In addition, the medical image displayed by the apparatus 100 according to an embodiment of the present invention may include 2D stereoscopic images 320, 330, and 340 indicating cross sections of the object 315.

As a reference, a stereoscopic imaging method is a method of respectively providing two different images to the left eye and the right eye of a user by taking disparity between the left eye and the right eye, and the stereoscopic images 310, 320, 330, and 340 shown in FIGS. 3A to 3C are to describe an image with a depth, which is recognized by both eyes of the user. Thus, the stereoscopic images 310, 320, 330, and 340 shown in FIGS. 3A to 3C may be different from a synthesized image of an image for the left eye and an image for the right image, which is actually displayed according to a stereoscopic imaging method.

The 2D stereoscopic image 320 indicates an image of a first cross section 312 of the object 315 shown in the 3D stereoscopic image 310. The 2D stereoscopic image 320 may be generated based on at least one of a direction, a gradient, and a depth of the first cross section 312. For example, the apparatus 100 may generate the 2D stereoscopic image 320 so that the user recognizes that the 2D stereoscopic image 320 is parallel to or has the same depth perception as the first cross section 312 of the 3D stereoscopic image 310.

The 2D stereoscopic image 330 indicates an image of a second cross section 313 of the object 315 shown in the 3D stereoscopic image 310. The 2D stereoscopic image 330 may be generated based on at least one of a direction, a gradient, and a depth of the second cross section 313. For example, the apparatus 100 may generate the 2D stereoscopic image 330 so that the user recognizes that the 2D stereoscopic image 330 is parallel to or has the same depth perception as the second cross section 313 of the 3D stereoscopic image 310.

The 2D stereoscopic image 340 indicates an image of a third cross section 314 of the object 315 shown in the 3D stereoscopic image 310. The 2D stereoscopic image 340 may be generated based on at least one of a direction, a gradient, and a depth of the third cross section 314. For example, the apparatus 100 may generate the 2D stereoscopic image 340 so that the user recognizes that the 2D stereoscopic image 340 is parallel to or has the same depth perception as the third cross section 314 of the 3D stereoscopic image 310.

Since the 2D stereoscopic images 320, 330, and 340 are generated and displayed based on the 3D stereoscopic image 310, the 2D stereoscopic images 320, 330, and 340 may rotate at the same angle according to rotation of the 3D stereoscopic image 310. Thus, according to the present invention, even when the 3D stereoscopic image 310 rotates, the user may easily and intuitively perceive a correlation (for example, a relative position of a cross section in the object 315) between the cross sections shown in the 2D stereoscopic images 320, 330, and 340 and the object 315 shown in the 3D stereoscopic image 310.

As shown in FIGS. 3A to 3C, the apparatus 100 may generate and display the 2D stereoscopic images 320, 330, and 340 including stereoscopic images of cross sections of the object 315.

According to another embodiment of the present invention, the apparatus 100 may generate and display a stereoscopic image of a curve-shaped cross section of the object 315. When the curve-shaped cross section of the object 315 is displayed as a non-stereoscopic image, since the curve-shaped cross section is displayed on a flat screen, it is difficult for the user to intuitively perceive the fact that the cross section has a curved surface. Thus, the apparatus 100 according to another embodiment of the present invention may display the stereoscopic image of the curve-shaped cross section of the object 315 in the form of a curved surface based on a direction, a gradient, and a depth of the 3D stereoscopic image 310 so that the user easily perceive a position relationship between the curve-shaped cross section of the object 315 shown in a 2D stereoscopic image and the object 315 shown in a 3D stereoscopic image.

Figure 4:
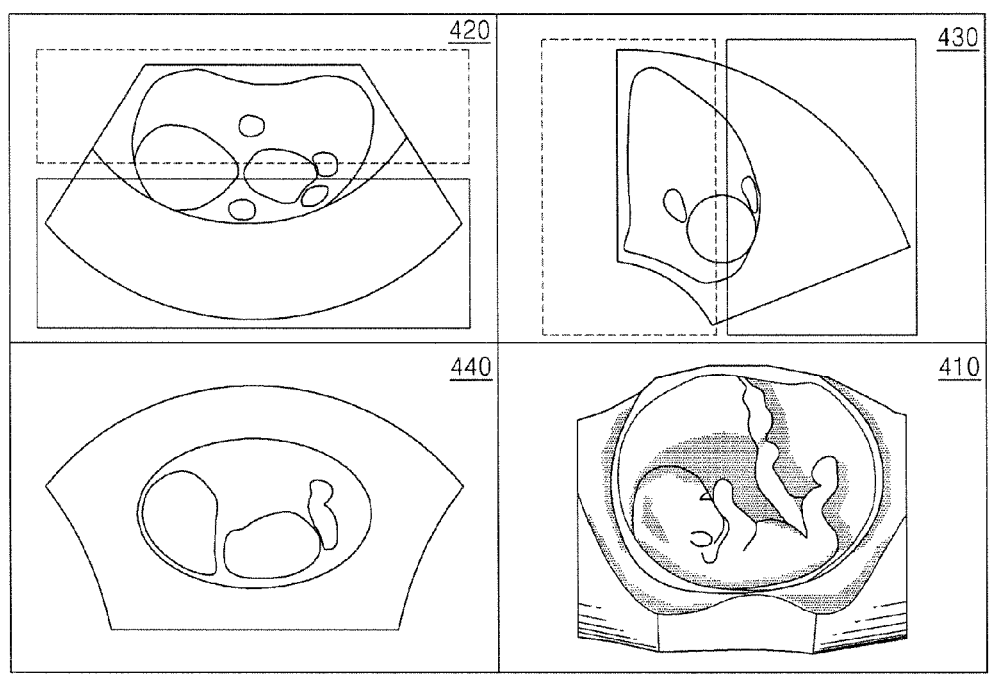
FIG. 4 illustrates a medical image displayed according to an embodiment of the present invention.

FIG. 4 illustrates a medical image displayed according to an embodiment of the present invention.

FIG. 4 shows a 3D stereoscopic image 410 of a fetus and 2D stereoscopic images 420, 430, and 440 indicating three cross sections regarding a coronal plane, a transverse plane, and a sagittal plane of the fetus, which are displayed according to an embodiment of the present invention.

According to an embodiment of the present invention, the apparatus 100 may generate the 2D stereoscopic images 420, 430, and 440 by taking the fetus shown in the 3D stereoscopic image 410 into account.

The 2D stereoscopic image 420 indicates the coronal plane of the fetus. The 2D stereoscopic image 420 corresponding to a position or direction of the fetus shown in the 3D stereoscopic image 410 is generated so that the user recognizes as if a portion marked with a dashed line were located inside a screen and a portion marked with a solid line were located outside the screen.

The 2D stereoscopic image 430 indicates the transverse plane of the fetus. The 2D stereoscopic image 430 corresponding to a position or direction of the fetus shown in the 3D stereoscopic image 410 is generated so that the user recognizes as if a portion marked with a dashed line were located inside a screen and a portion marked with a solid line were located outside the screen.

The 2D stereoscopic image 440 indicates the sagittal plane of the fetus. The 2D stereoscopic image 440 corresponding to a position or direction of the fetus shown in the 3D stereoscopic image 410 is recognized by the user as if the 2D stereoscopic image 440 were located at a same depth as a screen.

Thus, according to an embodiment of the present invention, the user may easily perceive that the 2D stereoscopic images 420, 430, and 440 indicate which cross sections of the fetus. In addition, when a cubic image of the fetus, which is viewed at a different angle by rotating the 3D stereoscopic image 410 of the fetus based on an input of the user, is displayed, the 2D stereoscopic images 420, 430, and 440 may also rotate in correspondence with the 3D stereoscopic image 410, thereby allowing the user to easily perceive a correlation between the 2D stereoscopic images 420, 430, and 440 and the 3D stereoscopic image 410.

In FIG. 4, the present invention has been described by illustrating the 3D stereoscopic image 410 of the fetus and the 2D stereoscopic images 420, 430, and 440 indicating three cross sections that are orthogonal to each other. However, 2D stereoscopic images of the present invention are not limited thereto. The medical image displayed in the present invention may include one 2D stereoscopic image or a plurality of 2D stereoscopic images. In addition, when the medical image displayed in the present invention includes a plurality of 2D stereoscopic images, the plurality of 2D stereoscopic images may be independent to each other, and may indicate arbitrary cross sections of an object or cross sections selected by the user.

The apparatus 100 according to an embodiment of the present invention may determine a type and the number of images to be displayed according to a user's input.

Figure 5:
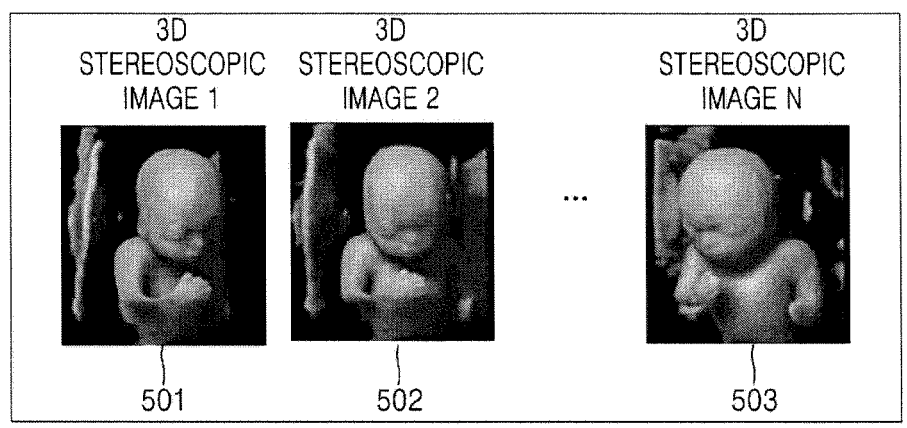
FIG. 5 illustrates a medical image displayed according to an embodiment of the present invention.

As shown in FIG. 5, the apparatus 100 may generate and display 3D stereoscopic images 501, 502, and 503 obtained by viewing an object at a plurality of angles. A type and the number of images to be displayed may be stored in advance in the memory (not shown) or may be newly input by the user. For example, the apparatus 100 may generate and display a cross-sectional stereoscopic image corresponding to 3D spatial coordinates in a 3D stereoscopic image of an object, which are input by the user, based on the 3D spatial coordinates. Thus, the cross-sectional stereoscopic image displayed according to the user's input may be an oblique cross-sectional image.

The method of displaying a medical image according to an embodiment of the present invention may include receiving an input of the user for changing a display image, and changing the display image based on the input of the user.

Figure 6:
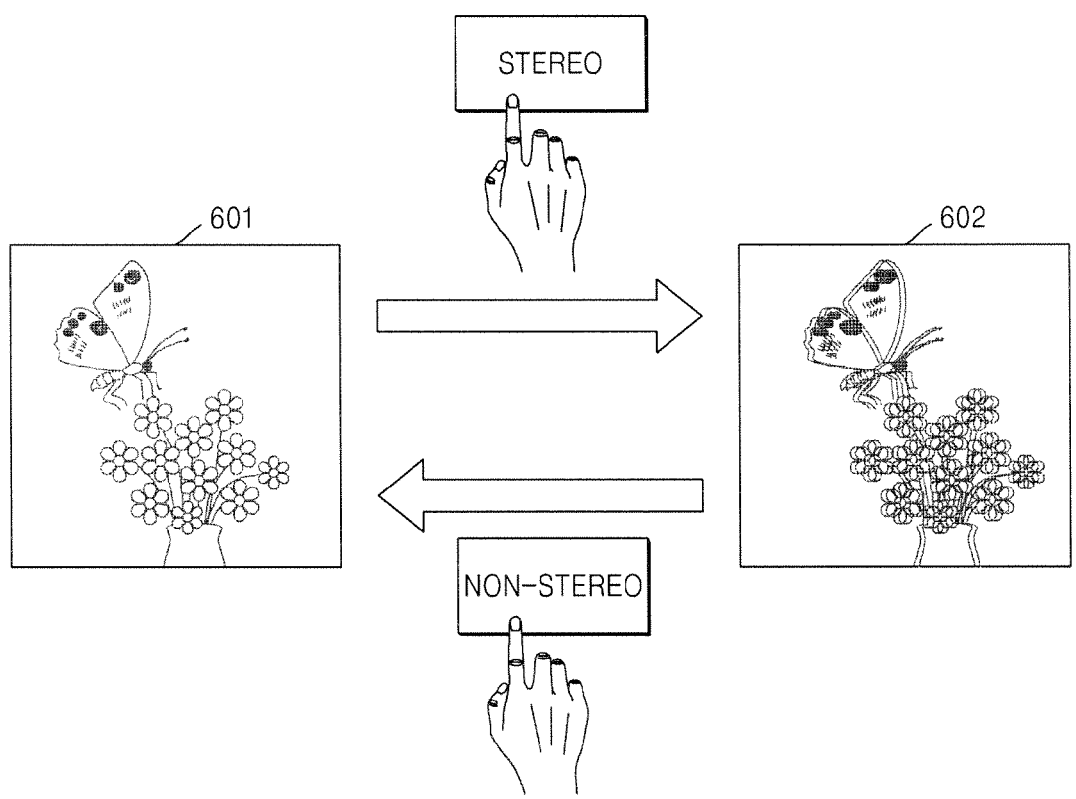
FIG. 6 illustrates a display image changed based on a user's input, according to an embodiment of the present invention.

FIG. 6 illustrates a display image changed based on a user's input, according to an embodiment of the present invention.

Referring to FIG. 6, while the apparatus 100 is displaying a stereoscopic image 602, if an external input for commanding to display a "non-stereoscopic image" instead of the stereoscopic image 602 is received, the apparatus 100 may display a non-stereoscopic image 601 corresponding to the stereoscopic image 602. While the apparatus 100 is displaying the non-stereoscopic image 601, if an external input for commanding to display a "stereoscopic image" instead of the non-stereoscopic image 601 is received, the apparatus 100 may display the stereoscopic image 602 corresponding to the non-stereoscopic image 601.

According to an embodiment of the present invention, the apparatus 100 may display a non-stereoscopic image to replace at least one image of a 3D stereoscopic image and a 2D stereoscopic image included in a medical image which is being displayed, based on an input of the user. On the contrary, apparatus 100 may display a stereoscopic image to replace at least one image of a 3D non-stereoscopic image and a 2D non-stereoscopic image included in a medical image, which is being displayed.

For the apparatus 100 to display a 3D stereoscopic image from volume data of an object, a process of generating and combining a plurality of images is necessary.

Figure 7A:
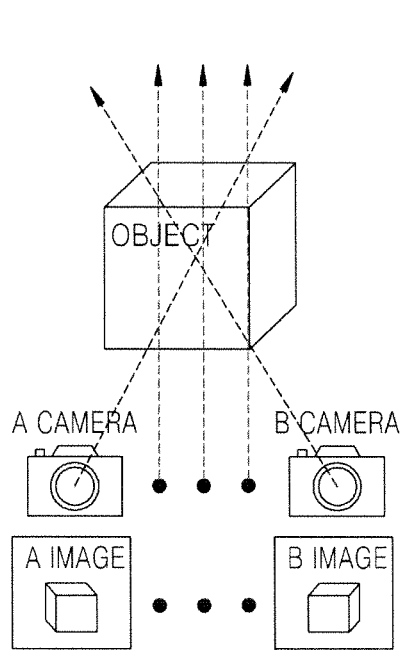
FIGS. 7A and 7B are conceptual diagrams for describing the method of displaying a medical image, according to an embodiment of the present invention.
Figure 7B:
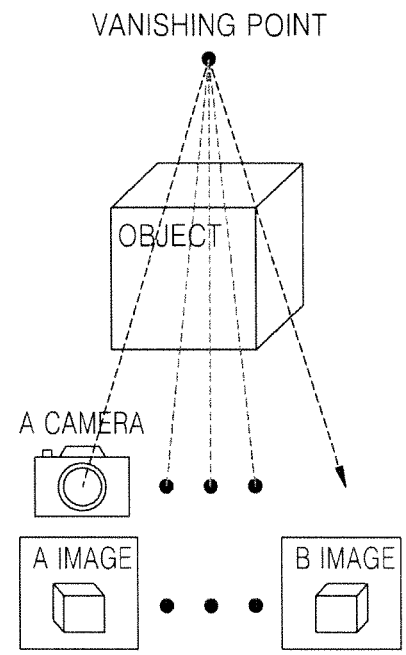

FIGS. 7A and 7B are conceptual diagrams for describing the method of displaying a medical image, according to an embodiment of the present invention.

As shown in FIG. 7A, to generate one 3D stereoscopic image, it is general to generate two images, i.e., a left image and a right image, by performing rendering at points of view of two or more virtual cameras. Thus, for a medical imaging apparatus to generate images of an object viewing at a plurality of angles, a rendering operation should be repeatedly performed, and in this case, a time required for a computation increases due to a break period taken until acquiring a next image after finishing one image acquisition operation.

However, as shown in FIG. 7B, the apparatus 100 according to an embodiment of the present invention may acquire a plurality of images by dividing a result generated by performing rendering at a point of view of one virtual camera to generate images of an object viewing at a plurality of angles. That is, the apparatus 100 may generate two images through one ray casting by setting one virtual camera in a virtual space where the object is located and dividing a direction of the ray casting into a front-to-back direction towards a vanishing point and a back-to-front direction from the vanishing point.

Thus, the apparatus 100 according to an embodiment of the present invention may reduce a break period taken until acquiring a next image after finishing one image acquisition operation and increase a computation speed in a graphics processing unit (GPU) computation process by defining one camera model and acquiring a plurality of images. That is, the apparatus 100 according to an embodiment of the present invention may reduce a data duplication, initialization, and synchronization time taken until performing a rendering operation by copying volume data of an object, which is stored in a central processing unit (CPU) to a GPU.

According to an embodiment of the present invention, an apparatus for displaying a medical image provides a stereoscopic image allowing a user to have depth perception so that the user intuitively perceives a bending degree, a relative position difference, a relative direction, and the like between components of an object.

While the present invention has been particularly shown and described with reference to exemplary embodiments thereof, it will be understood by one of ordinary skill in the art that various changes in form and details may be made therein without departing from the spirit and scope of the present invention as defined by the following claims. The exemplary embodiments should be considered in a descriptive sense only and not for purposes of limitation. Therefore, the scope of the present invention is defined not by the detailed description of the present invention but by the appended claims, and all differences within the scope will be construed as being included in the present invention.

What is claimed is:

1. A method performed by a medical image display apparatus, the method comprising:
   generating a three-dimensional (3D) stereoscopic image from volume data of an object, by an image generator of the medical image display apparatus, wherein the volume data of the object is acquired by a data acquisitor of the medical image display apparatus;
   generating at least one 2D stereoscopic image, by the image generator, based on at least one of a direction, a gradient, and a depth of a plane where a cross section of the object is located in the 3D stereoscopic image, wherein the at least one 2D stereoscopic image is parallel to or has a same depth as the plane; and
   displaying a medical image including the 3D stereoscopic image and the at least one 2D stereoscopic image in a stereoscopic imaging method, on a display screen of the medical image display apparatus,
   wherein the generating the 3D stereoscopic image comprises:
      performing a rendering of the volume data of the object at a point of view of one virtual camera of the medical image display apparatus;
      generating a plurality of images by dividing the rendered volume data of the object; and
      rendering a plurality of 3D stereoscopic images by setting the virtual camera in a virtual space where the object is located and changing a direction of ray casting towards the object from the virtual camera.

2. The method of claim 1, wherein the at least one 2D stereoscopic image indicates at least one cross section of the object.

3. The method of claim 1, further comprising receiving a user's input by a receiver of the medical image display apparatus; and
   generating a non-stereoscopic image corresponding to the 3D stereoscopic image and the at least one 2D stereoscopic image,
   wherein the displaying of the medical image comprises displaying a stereoscopic image instead of a non-stereoscopic image which is being displayed, or displaying a non-stereoscopic image instead of a stereoscopic image which is being displayed, based on the user's input.

4. The method of claim 1, further comprising generating a medical image including a non-stereoscopic image of the object.

5. The method of claim 1, wherein the displaying of the medical image comprises determining a type and the number of images to be displayed according to a user's input.

6. The method of claim 5, wherein the generating of the 3D stereoscopic image comprises generating a plurality of 3D stereoscopic images in which at least one of a direction, a gradient, and a depth of the object shown in the plurality of 3D stereoscopic images is different, and
   the displaying of the medical image comprises displaying at least one of the plurality of 3D stereoscopic images based on the user's input.

7. The method of claim 1, wherein the at least one 2D stereoscopic image includes a stereoscopic image of a cross section of the object, which is selected based on a user's input from the 3D stereoscopic image.

8. The method of claim 1, wherein the at least one 2D stereoscopic image includes stereoscopic images of three cross sections of the object, which are orthogonal to each other.

9. The method of claim 1, wherein the at least one 2D stereoscopic image includes a stereoscopic image of a curve-shaped cross section of the object.

10. An apparatus configured to display a medical image of an object, the apparatus comprising:
    a data acquisitor configured to acquire volume data of the object;
    an image generator configured to generate a three-dimensional (3D) stereoscopic image from the volume data of the object and at least one 2D stereoscopic image generated based on at least one of a direction, a gradient, and a depth of a plane where a cross section of the object is located in the 3D stereoscopic image, wherein the at least one 2D stereoscopic image is parallel to or has a same depth as the plane; and a display screen configured to display the medical image including the 3D stereoscopic image and the at least one 2D stereoscopic image in a stereoscopic imaging method, wherein the image generator renders the 3D stereoscopic image by:

performing a rendering of the volume data of the object at a point of view of one virtual camera of the medical image display apparatus;

generating a plurality of images by dividing the rendered volume data of the object; and rendering a plurality of 3D stereoscopic images by setting the virtual camera in a virtual space where the object is located and changing a direction of ray casting towards the object from the virtual camera.

11. The apparatus of claim 10, wherein the image generator generates the 2D stereoscopic image based on at least one of a direction, a gradient, and a depth of a plane corresponding to the cross section in the 3D stereoscopic image, and wherein the at least one 2D stereoscopic image indicates at least one cross section of the object.

12. The apparatus of claim 10, further comprising a receiver configured to receive a user's input, wherein the image generator further generates a non-stereoscopic image corresponding to the 3D stereoscopic image and the at least one 2D stereoscopic image, and the display screen displays a stereoscopic image instead of a non-stereoscopic image which is being displayed, or a non-stereoscopic image instead of a stereoscopic image which is being displayed, based on the user's input.

13. The apparatus of claim 10, wherein the image generator generates the medical image further including a non-stereoscopic image of the object.

14. The apparatus of claim 10, further comprising a receiver configured to receive a user's input, wherein the display screen determines a type and the number of images to be displayed according to a user's input.

15. The apparatus of claim 14, wherein the image generator generates a plurality of 3D stereoscopic images in which at least one of a direction, a gradient, and a depth of the object shown in the plurality of 3D stereoscopic images is different, and the display screen displays at least one of the plurality of 3D stereoscopic images based on the user's input.

16. The apparatus of claim 10, further comprising a receiver configured to receive a user's input, wherein the image generator generates the at least one 2D stereoscopic image including a stereoscopic image of a cross section of the object, which is selected based on a user's input from the 3D stereoscopic image.

17. The apparatus of claim 10, wherein the image generator generates the at least one 2D stereoscopic image including stereoscopic images of three cross sections of the object, which are orthogonal to each other.

18. The apparatus of claim 10, wherein the image generator generates the at least one 2D stereoscopic image including a stereoscopic image of a curve-shaped cross section of the object.

19. A non-transitory computer-readable storage medium having stored therein program instructions, which when executed by a computer, perform the method of claim 1.

* * * * *